United States Patent [19]

Abma et al.

[11] 3,991,085

[45] Nov. 9, 1976

[54] EPOXIDIZED DIALKYL PEROXIDES

[75] Inventors: Charles B. Abma, Davis; Ronald L. Friedman, San Rafael, both of Calif.

[73] Assignee: Argus Chemical Corporation, Brooklyn, N.Y.

[22] Filed: Dec. 26, 1974

[21] Appl. No.: 536,677

Related U.S. Application Data

[63] Continuation-in-part of Ser. No. 71,406, Sept. 11, 1970, abandoned.

[52] U.S. Cl. .................... 260/348 R; 260/45.8 A
[51] Int. Cl.[2] ............... C07D 303/24; C07D 303/22
[58] Field of Search ........................... 260/348 R

[56] References Cited

UNITED STATES PATENTS

| | | | |
|---|---|---|---|
| 3,117,166 | 1/1964 | Harrison et al. | 260/610 R |
| 3,214,422 | 10/1965 | Mageli et al. | 260/610 R |
| 3,558,665 | 1/1971 | Friedman et al. | 260/610 R |

Primary Examiner—Norma S. Milestone
Attorney, Agent, or Firm—Townsend and Townsend

[57] ABSTRACT

Dialkyl peroxides containing at least one epoxy grouping alpha to the peroxide linkage. Such peroxides have been found to be useful as catalysts in the preparation of heat cured polymer systems such as unsaturated polyester resins.

14 Claims, No Drawings

EPOXIDIZED DIALKYL PEROXIDES

The present invention relates to a new class of epoxidized dialkyl peroxides. Epoxidized acyl peroxides are disclosed in U.S. Pat. No. 3,558,665, issued Jan. 26, 1971. This is a continuation-in-part application of Ser. No. 71,406 filed Sept. 11, 1970, now abandoned.

The peroxides of this invention have special utilities by reason of their unusual chemical structures. The foremost of these results from the epoxy groups. Having both peroxy and epoxy groups, these new compounds are unique in that they are capable of both catalyzing and cross-linking with, for example, epoxy resins. In other applications, the presence of epoxy groups, which may be derived by oxidizing ethylenically unsaturated peroxides as disclosed hereinafter, contributes the advantageous properties of an acid scavenger and stabilizer to the epoxidized derivatives. Heretofore, it has been necessary to introduce acid scavengers and reaction stabilizers as separate additives to neutralize the acidic environment required during polymerization, for example, of vinyls. When employing the epoxy peroxides of this invention as catalysts, it is necessary to add little or none of such compounds.

Broadly, the polyfunctional epoxy peroxides of this invention are defined by the following structural formula:

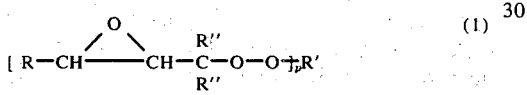
(1)

wherein $p$ is a whole number integer of from 1 to 2; R and R'' are separately selected from hydrogen or a monovalent hydrocarbon of up to 10 carbon atoms, preferably straight chained; and R' is a radical containing up to 30 carbon atoms, is attached to the peroxy linkage by a secondary or tertiary carbon atom and is selected from monovalent alkyl, aryl or arylalkyl, or comprises the divalent hydrocarbon group

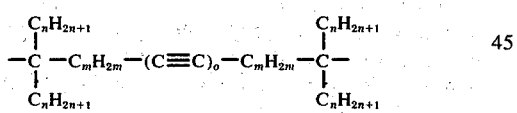

wherein $m$ is a whole number integer of from 0 to 5, preferably, 1 to 3, $n$ is a whole number integer of from 1 to 5, preferably 1 to 3, and $o$ is a whole number integer of from 0 to 1, being 1 when $m$ is 0. It is preferred that at least 2 of the R and R'' be hydrogen and that R' be up to 15 carbon atoms.

The epoxidized peroxides defined by this invention, therefore, include (1) those dialkyl epoxy-containing peroxides having the following structural formula:

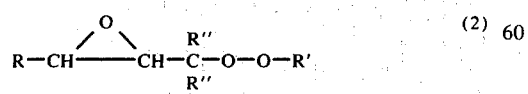
(2)

wherein R and R'' are as defined above and R' is a secondary or tertiary alkyl, aryl or arylalkyl group of 4 to 20 carbon atoms, preferably arylalkyl of 6 to 15 carbon atoms; and (2) those dialkyl epoxy-containing peroxides having the following structural formula:

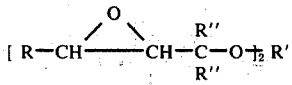
(3)

wherein R and R'' are defined as set forth supra, and R' is a divalent, branched chain hydrocarbon that is either saturated or contains an acetylenic linkage. In either of the aforementioned structural formulas it is preferred that R and R' be limited to hydrogen and carbon atoms.

Representative examples of epoxy peroxides within the scope of this invention include the following:

Cumyl Peroxy 2,3-Epoxy Propane

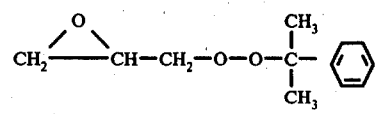

Cumyl Peroxy 2,3-Epoxy Pentane

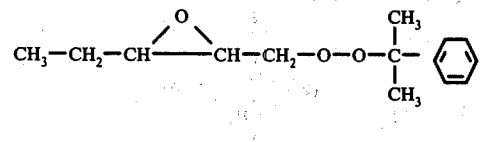

Cumyl Peroxy 2,3-Epoxy Decane

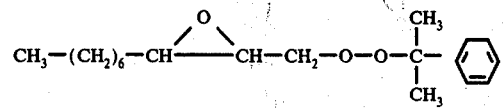

2,7-Dimethyl-2,7-Diperoxy(2,3-Epoxy Propyl) Octane

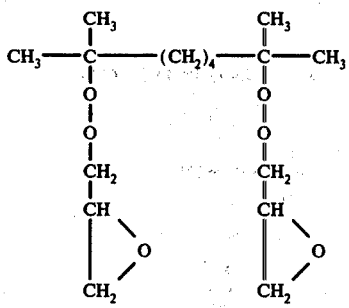

3,6-Dimethyl-3,6-Diperoxy(2,3-Epoxy Propyl) Octane

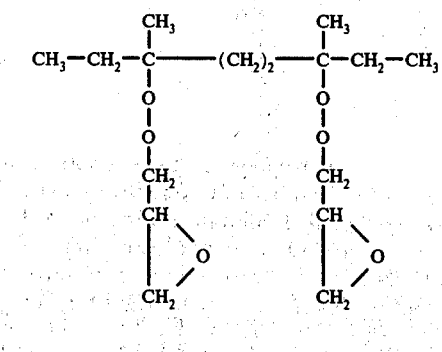

2,7-Dimethyl-2,7-Diperoxy(2,3-Epoxy Propyl) Octyne-4

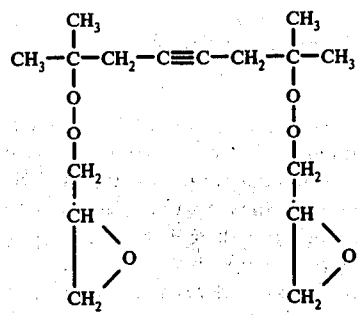

2,5-Dimethyl-2,5-Diperoxy(2,3-Epoxy Propyl) Hexyne-3

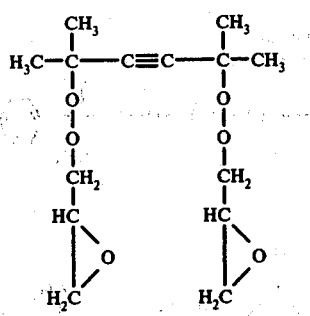

2,5-Dimethyl-2,5-Diperoxy(2,3-Epoxy Propyl) Hexane

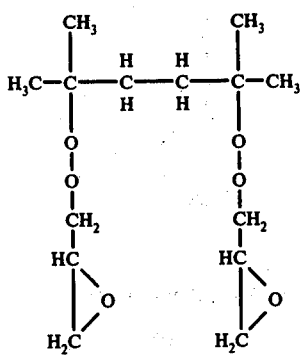

The novel epoxy peroxides of this invention can be obtained through a number of different processes. For example, an epoxy alkyl chloride can be reacted with an appropriate hydroperoxide, as set forth infra, in the examples. In addition, the compounds of this invention can be formed by oxidation of ethylenically unsaturated peroxide intermediates wherein the double bond

is converted to an epoxy grouping through a standard epoxidation reaction employing active oxygen agents such as peracetic acid, hydrogen peroxide/acetic acid with an acid catalyst, hydrogen peroxide/formic acid without an acid catalyst and the like.

The following examples are intended to be representative of the preparation of the novel compounds of this invention.

EXAMPLE I

Preparation of Tertiary-Butyl Peroxy 2,3 Epoxy Propane

To a three-neck round bottom flask fitted with thermometer, agitator and charging funnel was charged 121.0 grams of t-butyl hydroperoxide (75.36% - 1.0 mole) and 180.0 grams of water (10.0 moles). The mixture was cooled to 20° C using an external ice bath and 56.0 grams of potassium hydroxide (1.0 moles) was introduced. Thereafter, 92.5 grams of epichlorohydrin (2,3-epoxy propyl chloride) (1.0 moles) was added gradually over a period of about 30 minutes. The reaction, which was exothermic and required cooling, was allowed to proceed for six hours at a temperature of 30° C. Upon completion of the reaction, the mixture was cooled and allowed to phase separate and the aqueous phase discarded. The organic phase was washed twice with 100ml portions of 5 percent NaCl aqueous solution. The washed product was dried over anhydrous sodium sulfate, 89.6 grams of clear organic product was obtained (61% of theory).

Active Oxygen (by HI analysis) Found 10.06 Theory 10.96

Epoxy Oxygen (by HBr analysis) Found 10.50 Theory 10.96

GLC analysis indicated 94.6% purity with negligible amounts of starting reactants.

Sp. Gravity = 1.0919 at 25° C. Refractive Index = 1.4200 at 20° C.

EXAMPLE II

Preparation of 2,5-Dimethyl-2,5-Diperoxy (2,3-Epoxy Propyl) Hexane

To a three-neck round bottom flask fitted with thermometer, agitator and charging funnel was charged 56.1 grams of potassium hydroxide (0.5 moles) 50% aqueous and 60.0 grams of water (3.3 moles). The temperature was maintained at 20° C by external cooling and 51.5 grams of 2,5-Dimethylhexane 2,5-Dihydroperoxide, 87.5% (0.25 moles) was added. Finally, 46.8 grams of epichlorohydrin (2,3-Epoxy Propyl Chloride) (0.50 moles) was charged over a period of about 20 minutes. The reaction, which was exothermic and required cooling, was allowed to proceed for three hours at a temperature of 30° C. Upon completion of the reaction, the mixture was cooled and allowed to phase separate and the aqueous phase discarded. The organic phase was diluted with ether to aid phase separation and washed with equal portions of 5% potassium hydroxide aqueous solution, 3% sulfuric acid aqueous solution, and saturated sodium sulfate solution. The washed organic layer was filtered and vacuum stripped at 40° C (5mmHg).

Active Oxygen (KI method) Found 9.30% Theory 11.02%

Epoxy Oxygen (HBr analysis) Found 7.17% Theory 11.02%

GLC analysis indicated negligible amounts of epichlorohydrin.

Specific Gravity = 1.084 at 25° C. Refractive Index = 1.4625 at 20° C.

EXAMPLE III

Employing a similar technique to that utilized in Example II, the following products were also prepared.

| Compound | Active Oxygen Found % | Active Oxygen Theory % | Epoxy Oxygen Found % | Epoxy Oxygen Theory % | Specific Gravity at 25° C | Ref. Index at 20° C |
|---|---|---|---|---|---|---|
| Cumyl Peroxy 2,3 Epoxy Propane | 5.15 | 7.68 | 5.82 | 7.68 | 1.084 | 1.5148 |
| 2,5-Dimethyl-2,5-Diperoxy (2,3-Epoxy Propyl) Hexyne-3 | 8.01 | 12.58 | 4.00 | 12.58 | 1.078 | 1.4709 |
| 2,7-Dimethyl-2,7-Diperoxy (2,3-Epoxy Propyl) Octane | 8.52 | 10.05 | 5.75 | 10.05 | 1.063 | 1.4618 |

EXAMPLE IV

Polymerization Tests

A series of polymerization tests utilizing the Society of the Plastics Industry Standard Polyester Gel Test was conducted. In this test, 49.5 grams of a polyester resin and the selected amount of catalyst, such as 0.5 gram for a one percent test, are blended and placed in an oil bath maintained at constant temperature. Time to gel point, time to peak temperature, and the peak temperature were then recorded.

The unsaturated polyester resin tested was commercially available under the W. R. Grace Co. trade name MR4714 which contains styrene monomer as a cross-linking monomer. The bath temperature was maintained at 130° C (266° F) throughout the tests.

Representative data obtained is shown in the following Table I.

TABLE I

| Product | Gel Time | Peak Time | Peak Temp. ° C |
|---|---|---|---|
| 2,5-Dimethyl-2,5-Diperoxy (2,3-Epoxy Propyl) Hexyne-3 | 4'15'' | 4'46'' | 196 |
| 2,5-Dimethyl-2,5-Diperoxy (2,3-Epoxy Propyl) Hexane | 3'26'' | 3'52'' | 187 |
| t-Butyl Peroxy 2,3-Epoxy Propane | 7'00'' | 7'35'' | 184 |
| 2,7-Dimethyl-2,7-Diperoxy (2,3-Epoxy Propyl) Octane | 4'58'' | 5'28'' | 184 |
| Cumyl Peroxy 2,3-Epoxy Propane | 5'33'' | 6'00'' | 187 |

Similar polymerization was conducted with corresponding peroxides not having an epoxy grouping present therein. The data obtained is shown in the following Table II.

TABLE II

| Product | Gel Time | Peak Time | Peak Temp. ° C |
|---|---|---|---|
| 2,5-Dimethyl-2,5-di-tert-Butyl Peroxy Hexyne-3 | 9'30'' | 10'20'' | 181 |
| 2,5-Dimethyl-2,5-di-tert-Butyl Peroxy Hexane | 5'15'' | 5'44'' | 189 |
| di-tert-Butyl Peroxide | 6'10'' | 6'50'' | 189 |
| 1,4-di-tert-Butyl Peroxy Butane | 7'11'' | 7'51'' | 182 |

The improvement in gel time and peak time of the preferred groups of the novel compounds of this invention, i.e. when R' is arylalkyl or divalent was found to be particularly significant.

Although the foregoing invention has been described in some detail by way of illustration and example for purposes of clarity of understanding, it is understood that certain changes and modifications may be practiced within the scope of the appended claims.

What is claimed is:

1. An epoxidized peroxide consisting of carbon, oxygen and hydrogen atoms and having the formula

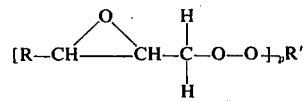

wherein p is a positive whole number integer of from 1 to 2, R is selected from hydrogen or alkyl of up to 10 carbon atoms, and R' is a radical of up to 15 carbon atoms composed of carbon and hydrogen atoms attached to the peroxy linkage through a tertiary carbon atom, said R' being selected from monovalent alkyl and arylalkyl radicals when p is 1 and the following divalent radical when p is 2

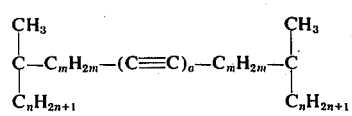

wherein m is a whole number integer selected from 0 to 5, n is a whole number integer of from 1 to 5, and o is a whole number integer of from 0 to 1, being 1 when m is zero.

2. An epoxidized peroxide in accordance with claim 1, wherein p is 1 and R' is arylalkyl.

3. An epoxidized peroxide in accordance with claim 1, wherein p is 1 and R is alkyl.

4. An epoxidized peroxide in accordance with claim 1, wherein $p$ is 2.

5. An epoxidized peroxide in accordance with claim 2, wherein R' is a cumyl radical and R is hydrogen.

6. An epoxidized peroxide in accordance with claim 2, wherein R' is a cumyl radical, R is ethyl, and R'' is hydrogen.

7. An epoxidized peroxide in accordance with claim 3, wherein R is $CH_3-(CH_2)_6-$.

8. An epoxidized peroxide in accordance with claim 3, wherein R' is t-Butyl radical and R is hydrogen.

9. An epoxidized peroxide in accordance with claim 4, wherein R is hydrogen and R' is

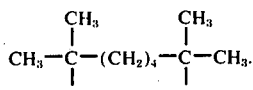

10. An epoxidized peroxide in accordance with claim 4, wherein R is hydrogen and R' is

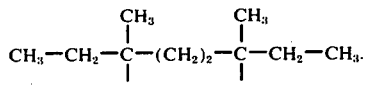

11. An epoxidized peroxide in accordance with claim 4, wherein R is hydrogen and R' is

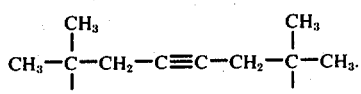

12. An epoxidized peroxide in accordance with claim 4, wherein R is hydrogen and R' is

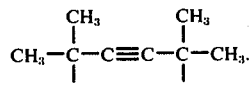

13. An epoxidized peroxide in accordance with claim 4, wherein R is hydrogen and R' is

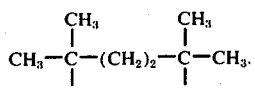

14. An epoxidized peroxide in accordance with claim 1, wherein $m$ and $n$ are 1 to 3.

* * * * *